United States Patent [19]
Bottone et al.

[11] Patent Number: 6,090,613
[45] Date of Patent: *Jul. 18, 2000

[54] BACILLUS PUMILUS STRAIN

[75] Inventors: Edward J. Bottone, Irvington, N.Y.; Richard Peluso, New York, N.Y.

[73] Assignee: Mount Sinai School of Medicine of the City University of New York, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/840,419

[22] Filed: Apr. 29, 1997

Related U.S. Application Data

[63] Continuation of application No. 08/478,962, Jun. 7, 1995, abandoned.

[51] Int. Cl.⁷ ......................................................... C12N 1/20
[52] U.S. Cl. ........................................................... 435/252.5
[58] Field of Search .......................................... 435/252.5

[56] References Cited

PUBLICATIONS

Selitrennikoff, C. P. , Screening for Antifungal Drugs, in *Biotechnology of Filamentous Fungi*, Finkelstein, D., and Ball, C., eds., Butterworth–Heinemann, Boston, 1992.
Gootz, T. D. , Clin. Microbiol. Rev. 3:13–31, 1990.
Kuhn, P.J. , Pestic. Sci. 25:123–35, 1989.
Ronald, A.R. , Clin. and Invest. Med. 12:3–6, 1989.
Espinel–Ingroff, A. et al., Eur. J. Clin. Microbiol. Infect. Dis. 8:352–61, 1989.
Bossche, H. V. et al., Crit. Rev. Microbiol. 15:57–72, 1987.
Ōmura, S., Microbiol. Rev. 50:259–79, 1986.
Ryley, J.F. et al., Adv. Pharm. Chemother. 18:49–176, 1981.
Lebbadi et al., J. Appl. Bacteriol. 77:49–53, 1994.
Kugler et al., Arch. Microbiol. 153:276–281, 1990.
Besson et al., Microbios 62:93–99, 1990.
Oki et al., J. Antibiotics 42:1756–1762, 1989.
Peypoux et al., J. Biochem 118:323–327, 1981.
Majumdar et al., Nature 181: 134–135, 1958.
Raubitschek et al., Dermatologica 100:45–49, 1950.
Walton et al., J. Clin Invest. 28:924–926, 1949.
Hutchins, A.S. , *Microb. Ecol.* vol. 6, p. 253–259, 1980.
Konishi et al., J. of Antibiot., vol. 42, p. 1749–1755, 1989.
Tschet et al, Proc. Natl. Sci. Counc. B. Roc., vol. 13, p. 258–261, 1989.
Wakayama et al., Antimicrob. Agents Chemotherapy, p. 939–940, 1984.
Stabb, E.V., et al. Appl. Enivron. Microbiol. 60:4404–4412, 1994.

*Primary Examiner*—Irene Marx
*Attorney, Agent, or Firm*—Baker & Botts, L.L.P.

[57] ABSTRACT

The present invention relates to an antifungal agent obtained from a bacterium, *Bacillus sinaii*. It is based, at least in part, on the discovery that in mixed cultures of the bacterium and various fungi, zones of inhibition of fungal growth were found in the regions surrounding colonies of the Bacillus bacteria. In various embodiments, the present invention provides for the novel Bacillus bacterium, which has been purified and isolated from other organisms; for compositions comprising the antifungal agent produced by said Bacillus bacterium; and for methods of inhibiting fungal growth comprising exposing a fungus to an effective concentration of the antifungal agent.

1 Claim, 6 Drawing Sheets

BACILLUS PUMILUS STRAIN

This application is a continuation of application Ser. No. 08/478,962, filed on Jun. 7, 1995, now abandoned.

INTRODUCTION

The present invention relates to an antifungal compound produced by a bacterium of the Bacillus genus.

BACKGROUND OF THE INVENTION

Fungal infections constitute life-threatening infections in immunocompromised patients, including persons suffering from AIDS or cancer as well as patients whose immune systems are suppressed or damaged by chemical agents or radiation. Among the most dangerous fungal pathogens are Mucor and Aspergillus species.

Mucor infections present serious consequences to immunocompromised patients, and particularly, to diabetics, who often develop infection of the paranasal sinuses, with extension into the brain (rhinocerebral). Orbital infection may spread to involve the eye as well. Other complications include spread to the lung, skin and gastrointestinal tract.

Aspergillus infections present primarily as pulmonary complications in immunocompromised patients, often resulting in a necrotizing pneumonia, with widespread dissemination to other organs.

Both Mucor and Aspergillus infections may result in blood vessel infarction. High mortality rates are associated with both infections.

Currently, the only agent available for treating Mucor or Aspergillus infections is Amphotericin B. Amphotericin B, derived from *Streptomyces nodosus*, has a number of adverse side effects associated with its use, including anaphylaxis, thrombocytopenia, and generalized pain. Renal function is impaired in over 80% of patients given amphotericin B (*The Pharmacological Basis of Therapeutics*, Goodman, A. G. et al., eds., Macmillan Publishing Co., New York, 1985).

SUMMARY OF THE INVENTION

The present invention relates to an antifungal agent obtained from a bacterium, *Bacillus pumilus* MSH. It is based, at least in part, on the discovery that in mixed cultures of the bacterium and various fungi, zones of inhibition of fungal growth were found in the regions surrounding colonies of the Bacillus bacteria.

In various embodiments, the present invention provides for the novel Bacillus bacterium, which has been purified and isolated from other organisms; for compositions comprising the antifungal agent produced by said Bacillus bacterium; and for methods of inhibiting fungal growth comprising exposing a fungus to an effective concentration of the antifungal agent.

DETAILED DESCRIPTION OF THE INVENTION

Figure 1:
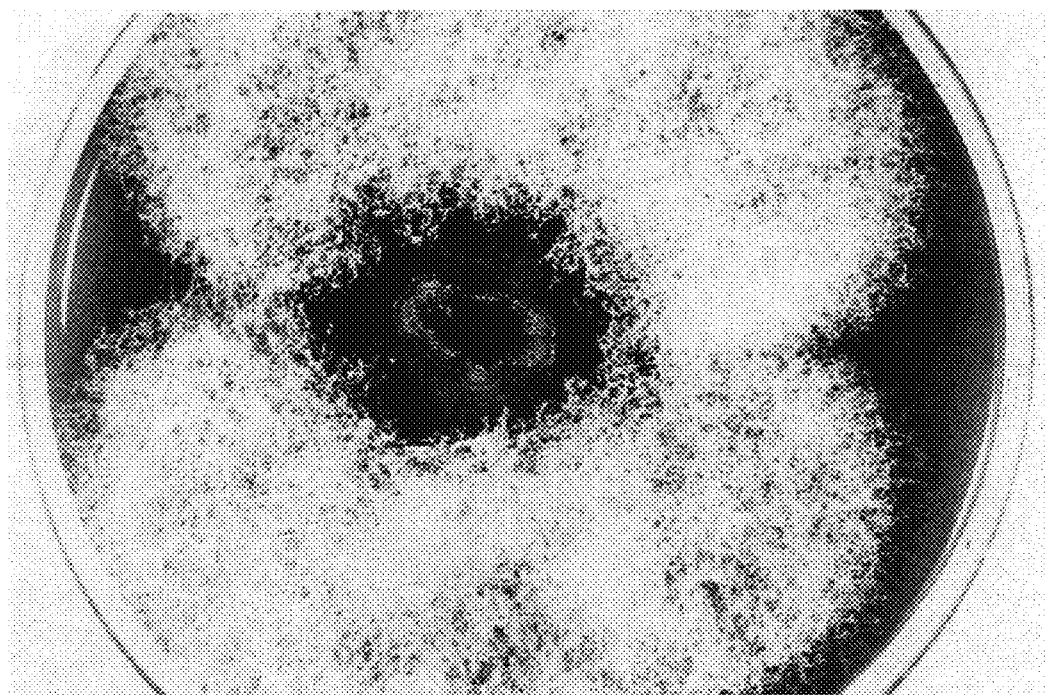
FIG. 1. A zone of inhibition in a lawn of Mucor fungus surrounds a spot-inoculum of *Bacillus pumilus* MSH.

The present invention provides, first, for a novel bacterium of the Bacillus genus which produces an anti-fungal compound. Prior to the invention, no Bacillus species had been observed to produce an anti-fungal compound. The bacterium of the invention is a gram-positive, spore-forming bacterium of the genus Bacillus. It may be identified by plating co-cultures of the bacteria and Mucor or Aspergillus fungi onto a sheep blood agar plate and identifying a hemolytic bacterial colony surrounded by a zone of inhibition of fungal growth. In a preferred embodiment, the present invention provides for a purified and isolated bacterium which produces an agent having the aforementioned antifungal activity, and which has been deposited, on Sep. 1, 1995 as a purified bacterial culture, with the American Type Culture Collection, and assigned Accession Number 55707. The address of the American Type Culture Collection is 10801 University Boulevard, Manassas, Va. 20110-2209. The bacterium of the invention is referred to, hereinafter, as the *Bacillus pumilus* MSH.

The present invention also provides for the antifungal compound produced by *Bacillus pumilus* MSH. Such antifungal compound has a molecular weight between about 500 and 3000 daltons, as measured by dialysis tubing and membrane filters of defined pore sizes, and has been observed to be protease resistant, chloroform resistant, chloroform and ethyl acetate soluble, and stable, in agar, at 4° C., 25° C., and 37° C. for a minimum of 14 days.

The antifungal compound of the invention may be purified from cultures of the *Bacillus pumilus* MSH bacteria using standard laboratory techniques, and is substantially free of bacterial contaminants. Sterile-filtered broth from overnight cultures may be concentrated with the use of filters and dialysis tubing of defined pore sizes. For example, a sterile preparation of the antifungal compound may be prepared by culturing *Bacillus pumilus* MSH bacteria in broth and then passing the broth through a 0.45 micron sterile membrane filter. In another approach, dialysis against ammonium acetate, followed by lyophilization, yields a residue which may be reconstituted in fresh broth. Alternatively, overnight broth may be extracted with organic solvents, such as chloroform or ethyl acetate, for example. The resulting organic phase may be lyophilized, and the residue dissolved in fresh broth.

Assays for monitoring antifungal activity may be performed by adding serial dilutions of a concentrated broth to wells in a microtiter plate, followed by the addition of spores from a candidate fungus to be tested. Following incubation at the appropriate temperature, wells may be examined microscopically to determine if spore germination has occurred. Antifungal activity may be identified by the inhibition of spore germination.

The nature of the antifungal compound may be identified by protease treatment (e.g., protease K) of a concentrated broth to determine if activity is retained. Following such treatment of the broth, organic extraction and reconstitution may be performed, and if antifungal activity is retained, the compound may be characterized as non-proteinaceous. Further characterization of a non-proteinaceous compound, such as that derived from *Bacillus pumilus* MSH, may be performed, for example, by concentration of the activity, as described above, followed by reconstitution in ammonium acetate, and subsequent fractionation of the material by high-performance liquid chromatography (HPLC). HPLC analysis may utilize a C-18 column developed in ammonium acetate or an increasing gradient of methanol in ammonium acetate. Antifungal activity assays of column fractions may be used to locate the active fraction.

Following HPLC analysis, structural determination may be performed, for example, by mass spectroscopy of the purified compound.

Accordingly, the present invention provides for sterile compositions comprising partially or substantially purified antifungal compound, in a pharmaceutically suitable carrier, including, but not limited to, water, saline, or alcohol. The antifungal compound of the invention may also be comprised in a micelle, microsphere, liposome, or sustained-release device such as, but not limited to, a gel or wax matrix.

The present invention still further provides for a method for inhibiting the growth of a fungus comprising exposing the fungus to an effective concentration of the antifungal compound, as produced by *Bacillus pumilus* MSH bacteria. For example, and not by way of limitation, the antifungal compound may be used to inhibit the growth of mold-like fungi, comprising members of the genera Mucor, Rhizopus, Absidia, Cunninghamella, and Aspergillus and, to a lesser extent, yeast-like fungi, such as *Cryptococcus neoformans* and Candida species.

In particular embodiments, the antifungal compound may be used for the treatment of a fungal infection in a subject in need of such treatment, such as an immunocomprised human subject. The effective concentration of antifungal compound for such treatment may be determined using standard techniques for evaluating the dose response relationship between the concentration of antifungal compound and antifungal effect for a particular fungal pathogen. The antifungal agent may be administered topically, by nasal spray, eye drops, inhalation, intravenously, orally, subcutaneously, etc.

The antifungal compound of the invention may also be used to inhibit the growth of fungi in eukaryotic or prokaryotic cell culture, or may be utilized in cleaning compositions or industrial applications.

EXAMPLE: IDENTIFICATION OF AN ANTIFUNGAL ACTIVITY PRODUCED BY A BACILLUS

Fungicidal activity produced by a Bacillus species was first noted to occur on a sheep blood agar plate touch-inoculated with a synthetic sponge contaminated with the Bacillus bacteria and Mucor. Wherever a hemolytic Bacillus colony developed on the agar surface, a zone of inhibition of Mucor growth was observed.

Bacteria from the aforementioned colonies were purified and isolated, and observed to be gram-positive, spore-forming bacteria, apparently of the genus Bacillus (*Bacillus pumilus* MSH).

The antifungal activity of the bacteria was demonstrated by spot-inoculating a purified culture of the bacteria onto lawns of Mucor, Aspergillus, prepared by inoculating the surface of a 5% sheep blood agar plate. Upon examination of the plates after 24 hours of incubation at 37° C., zones of growth inhibition of the fungi in the regions of bacterial inoculation were observed. For example, FIG. 1 shows the results of one such experiment, where bacteria were inoculated onto a lawn of Mucor and incubated for 24 hours; the zone of inhibition of fungal growth is clearly apparent. In other experiments, some growth inhibition of *Cryptotoccus neoformans* and Candida by *Bacillus pumilus* MSH was observed.

Figure 2:
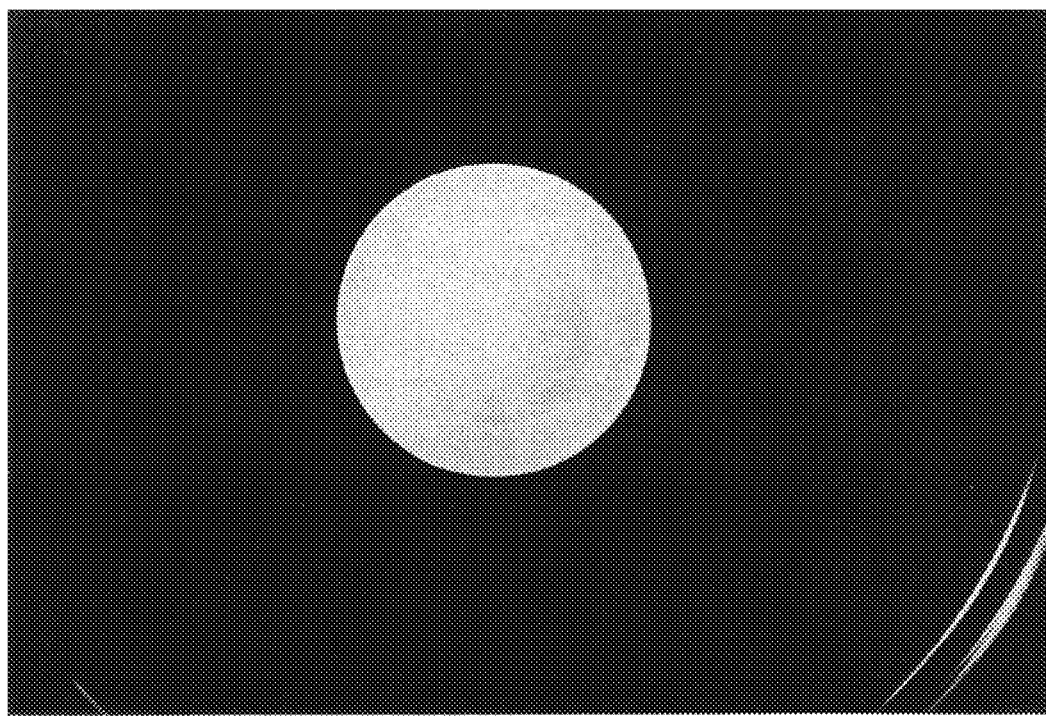
FIG. 2. *Bacillus pumilus* MSH was cultured in agar on a 0.45 micron sterile membrane filter (white disc), placed on the surface of a blood agar plate.
Figure 3:
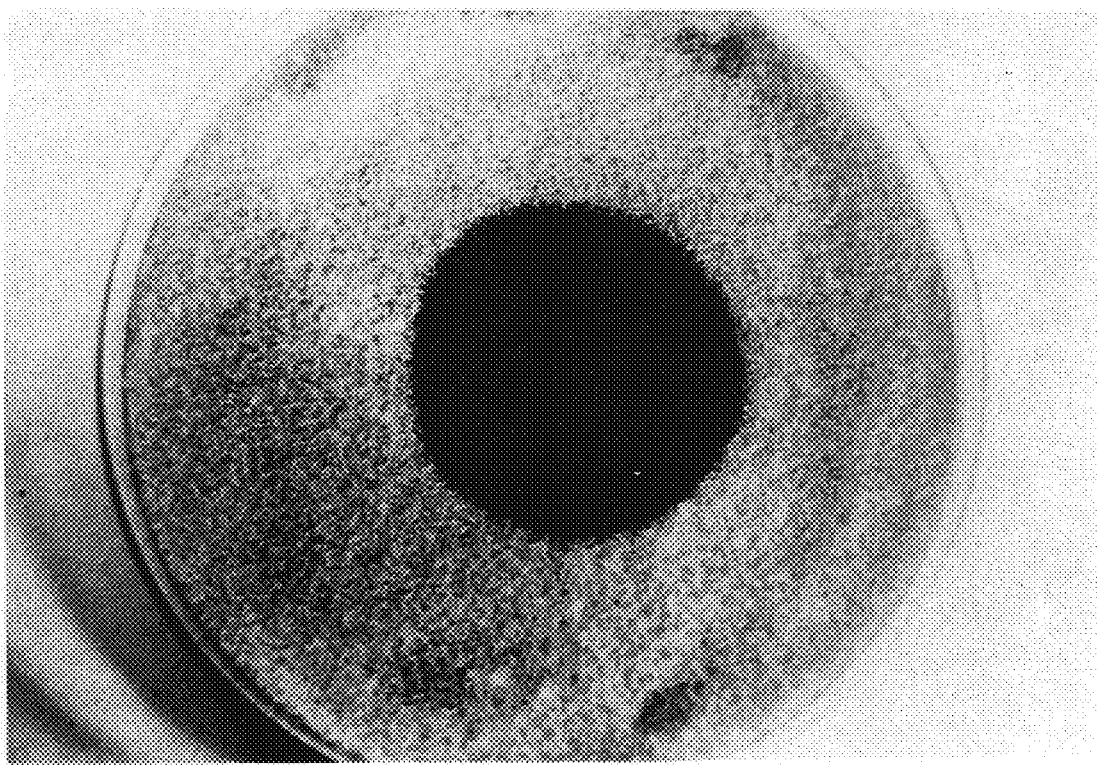
FIG. 3. The *Bacillus pumilus* MSH bearing filter disc shown in FIG. 2 was removed, and the blood agar plate was flooded with spores of Mucor and reincubated for 24 hours. Note the zone of inhibition of fungal growth in the area of agar which had been covered with the filter membrane.

The existence of a diffusible antifungal compound was further demonstrated by experiments in which the bacteria were grown, in agar, on a 0.45 micron sterile filter placed on the surface of a blood agar plate (FIG. 2). After 24 hours of incubation, the membrane was removed and the underlying agar surface was flooded with spores of Mucor or Aspergillus, and the plate reincubated. Twenty-four hours later, a large zone of inhibition of fungal growth was observed where the cell-free antifungal compound had diffused through the membrane filter; FIG. 3 shows such a zone of inhibition in a lawn of Mucor occurring at the position of the filter shown in FIG. 2.

The antifungal effect was further observed to inhibit the growth of Mucor and Aspergillus fungi when the bacteria of the invention were simultaneously co-cultivated with these fungi in liquid broth medium.

The antifungal compound appears to be truly fungicidal, as viable fungal organisms have not been recovered from subcultures of fungal inoculum within the zone of inhibition. Furthermore, secondary backgrowth of fungus within the zone of inhibition has not been observed to occur after 14 days of continued incubation.

Figure 4:
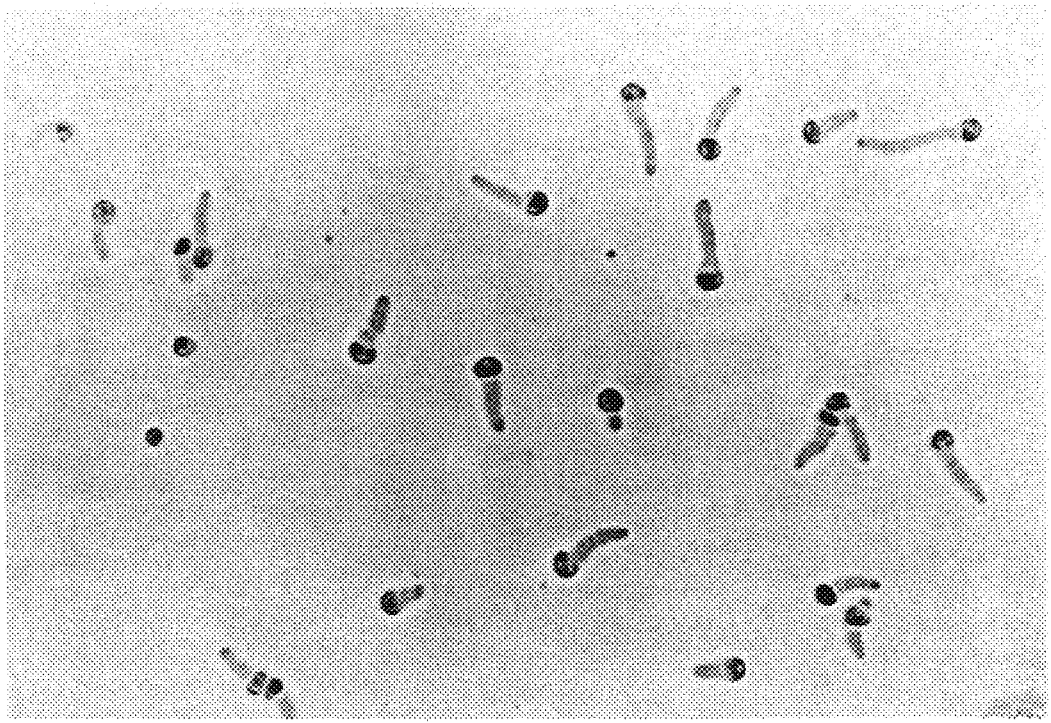
FIG. 4. Inhibition of Mucor hyphal elongation by active principle from *Bacillus pumilus* MSH, subsequent to spore germination.
Figure 5:
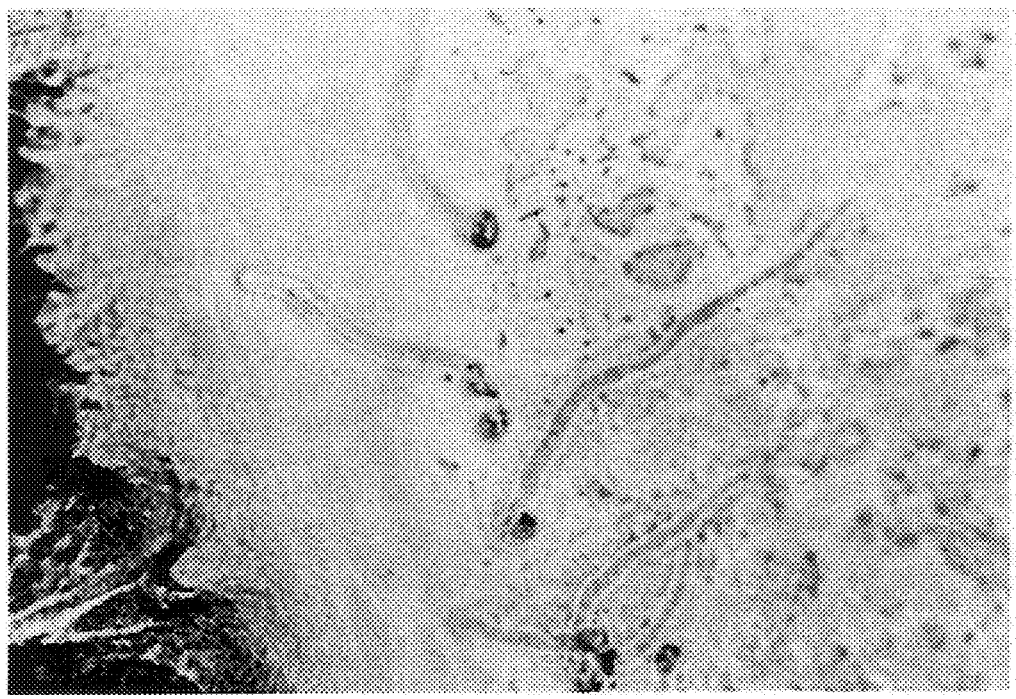
FIG. 5. Aborting of Mucor hyphal extensions from germinating spore exposed to *Bacillus pumilus* MSH colony at left (magnified 1,000×).
Figure 6A:
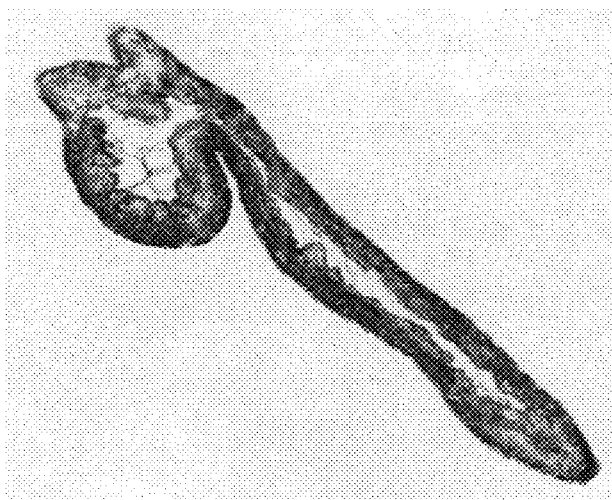
FIG. 6A is an electron micrograph of normal Mucor spore germination by hyphal extension (magnified 5,000×).
Figure 6B:
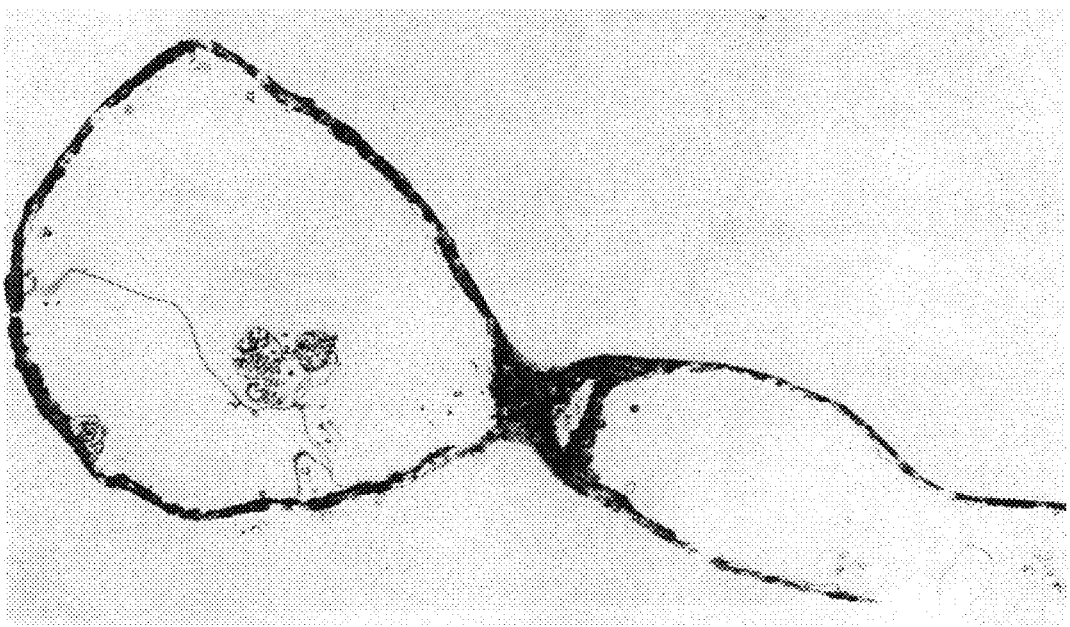
FIG. 6B is an electron micrograph of Mucor spore exposed to *Bacillus pumilus* MSH, showing aborted rudimentary hyphal element. Clear areas on membrane denote lesions (magnified 33,000×).

Without being restricted as to any theory, the antifungal compound of the invention appears to operate by inhibiting elongation (growth) of fungal hyphae subsequent to spore germination. FIG. 4 is a photomicrograph showing inhibition of Mucor hyphal elongation by the active principle of *Bacillus pumilus* MSH subsequent to spore germination. FIG. 5 shows the aborting of Mucor hyphal extensions from germinating spores which were exposed to a colony of *Bacillus pumilus* MSH. Electron microscopy studies have suggested that the antifungal compound exerts a lytic activity against fungal hyphae. FIG. 6A is an electron micrograph showing normal Mucor spore germination by hyphal extension. FIG. 6B is an electron micrograph of a Mucor spore which was exposed to the antifungal compound of *Bacillus pumilus* MSH, showing an aborted rudimentary hyphal element devoid of internal structure. Lesions in the membrane are denoted by the clear areas.

EXAMPLE: CHARACTERIZATION OF ANTIFUNGAL COMPOUND

Sterile-filtered broth from overnight growth of *Bacillus pumilus* MSH was concentrated using filters and dialysis tubing with defined pore sizes. This analysis led to the conclusion that the active compound was of greater than 500 molecular weight and less than 3,000 molecular weight. The concentration of the active compound in an overnight broth was low, so that concentration proved necessary. Concentration was performed in two ways; first, overnight broth was dialyzed against 0.15M ammonium acetate using tubing with a 500 MW pore size. The dialysate was then dried by lyophylization, and the residue was reconstituted in fresh broth. Alternatively, overnight broths were extracted by vigorous mixing with either chloroform or ethyl acetate. The resulting organic phase was then dried, and the residue was dissolved as above. Both of these methods appeared to be capable of concentrating the activity. Assays for activity were performed in microwell plates. The concentrated broths were diluted serially in fresh broth, and then spores of Mucor were added to each well. After incubation at 37° C., wells were examined microscopically, and inhibition of spore germination was evident in the wells with the highest concentration of overnight broth concentrate, with aborted germination evident as dilution occurred. The spores in the first few wells were removed and plated, but failed to germinate, indicating that the compound is fungicidal, rather than fungistatic. In another experiment sterile-filtered overnight broths were treated with protease K, 70 $\mu$g/ml for 2 hours at 37° C., followed by extraction with chloroform and subsequent lyophylization of the organic layer. This procedure yielded as much activity as was recovered from non-treated broths, indicating that the active compound was probably not a protein.

A purified culture of the bacteria of the invention has been deposited with the American Type Culture Collection (ATCC), 10801 University Blvd, Manassas, Va. 20110-2209, on Sep. 1, 1995 and assigned Accession Number 55707.

Various publications are cited herein, the contents of which are hereby incorporated by reference in their entirety.

What is claimed is:

1. A biologically pure culture of *Bacillus pumilus* MSH, ATCC 55707, which produces a compound having antifungal activity against a fungus of the genus Mucor or Aspergillus in a recoverable amount in an aqueous nutrient medium containing assimilable sources of carbon, nitrogen and inorganic substances.

* * * * *